United States Patent [19]

Numata

[11] Patent Number: 5,369,130
[45] Date of Patent: Nov. 29, 1994

[54] PASTE COMPOSITION FOR SKIN BARRIER

[75] Inventor: Satoru Numata, Tokyo, Japan

[73] Assignee: Alcare Co., Ltd., Tokyo, Japan

[21] Appl. No.: 8,477

[22] Filed: Jan. 25, 1993

[30] Foreign Application Priority Data

Jan. 27, 1992 [JP] Japan ................... 4-035629

[51] Int. Cl.$^5$ ................... A61K 9/06; A61L 25/00
[52] U.S. Cl. ................... 514/772.3; 424/78.02; 523/105; 524/491; 524/492; 524/502; 514/969
[58] Field of Search ................... 514/772.3, 772.4, 969; 424/447, 449, 485, 486, 78.02; 523/105; 524/847, 502, 491, 492

[56] References Cited

U.S. PATENT DOCUMENTS

| | | | |
|---|---|---|---|
| 4,222,923 | 9/1980 | Rhodes et al. | 524/292 |
| 4,830,776 | 5/1989 | Thompson | 524/43 |
| 5,176,915 | 1/1993 | Hoffmann | 424/449 |

Primary Examiner—G. S. Kishore
Assistant Examiner—Peter F. Kulkosky
Attorney, Agent, or Firm—Haverstock, Garrett & Roberts

[57] ABSTRACT

Skin barrier paste compositions free from organic solvents comprised of at least a rubber component and a filler component wherein the rubber component includes a liquid rubber having an average molecular weight of about 1,000 to about 80,000 and a viscosity of about 200 poise to about 6,000 poise at 40° C., the rubber component being present in the paste composition in the range of about thirty percent to about seventy percent by weight. The present inventive paste compositions can be freely formed with the fingertips or a spatula; they are less irritating to the skin, mucosa and/or the injured area; and they are less susceptible to a viscosity change when exposed to the atmosphere, thus assuring an ease of application and a stable paste formulation when stored in a container.

3 Claims, No Drawings

PASTE COMPOSITION FOR SKIN BARRIER

Applicant hereby claims foreign priority benefits under 35 USC §119 of corresponding Japanese patent application Serial No. (Hei) 4-35629, filed Jan. 27, 1992.

FIELD OF THE INVENTION

The present invention relates to skin barrier paste compositions which are used to protect the skin surface adjacent stomas or openings from inside the body or body surface from which materials are excreted or exudated. Specifically, such paste compositions protect the skin surface in proximity to devices, such as an artificial anus, an artifical bladder, a digestive organ fistula, a urinary fistula, a tracheal fistula, or openings associated with injury or drainage by surgical treatment. In addition, the paste compositions remain in a paste consistency and stably secure the means fitted for treatment by affecting the texture of the skin surface.

BACKGROUND OF THE INVENTION

Conventionally, patients having an artificial anus, artifical bladder, digestive organ fistula, urinary fistula, tracheal fistula, injury or drainage by surgical treatment, wear a pouch on the skin around the opening, for example, around the excretion or exudation area. The pouch is affixed to the skin with the help of a sensitive adhesive plate so as to temporarily store the excretion or excudation in the pouch. The adhesive plate allows one to subsequently replace the pouch with a new one at a proper interval, such as when full.

However the circumferential area of the opening can have a complicated shape and it can be almost impossible to cut and attach the sensitive adhesive plate in a shape identical to that of the opening area so that a gap can be unavoidably created between the skin and the sensitive adhesive plate. The gap thus formed is likely to be exposed to excreted material or exudation resulting in a dermatitis or a skin irritation. In addition, the skin surface adjacent the opening is not consistently even, particularly because of the presence of an operative wound, hernia, depression or cicatrix, and as a result, the seal between the sensitive adhesive plate and the skin becomes irregular and uneven and causes leakage due to the inadequate sealing.

To solve these problems various paste compositions have been developed including karaya paste, such as BIOPLASTPASTE by ALCARE Co., prepared by making karaya gum into a paste-like state using polyhydric alcohol; a paste composition prepared by blending silica and hydrocolloids such as karaya gum, carboxymethylcellulose (CMC), gelatin, pectin, and the like with polyvinylpyrrolidone (PVP) containing alcohol in amounts of 50%, such as GANTREZ by GAF Corporation; and a paste comprising a mixture of water-absorbing granular hydrocolloid gum, colloidal silica, and a solution of a tacky film forming resin and an organic solvent, as disclosed in Japanese Examined Patent Application Publication No. Sho 60-47856, corresponding to Great Britain Patent No. 2,062,663. These conventional paste compositions have been effective in filling the gap between the circumference of the body opening and the sensitive adhesive plate, in covering the skin exposed, and in flattening the area to which the sensitive adhesive plate is attached, thereby improving the sealing effect by smoothing the rough surface of the skin. All these paste compositions, however, contain an organic solvent, which irritates the skin, mucosa and/or the wound or injured area through the contact thereof and causes pain and discomfort. At best, the solvent related pain ceases when the organic solvent vanishes such as by evaporation, but in a worse case such compositions can eventually cause inflammation or dermatitis. In addition, these prior paste compositions are difficult to maintain in a proper paste-like fluid form. Treatments then must be done promptly because when the organic solvent contained therein evaporates, the paste viscosity increases and the composition becomes unworkable. Treatments thus must be repeated if the application of the paste is done unsatisfactorily or requires too much time, such as when applications involve complicated shapes or those applying the paste have inadequate experience. Also, the past compositions solidify at the outlet of the paste container, hindering easy handling and convenience upon subsequent use. Furthermore, once applied the prior paste compositions are difficult to remove smoothly, which results in a significant loss of time and increased pain to the patient.

SUMMARY OF THE INVENTION

The object of the present invention is to provide paste compositions which act as skin barriers that can be freely formed and applied with the finger tips or spatulas and are less irritating to the patient's surrounding skin, mucosa and/or injured area. A further object is to provide a paste composition which is less susceptible to viscosity change when exposed to the atmosphere, thus allowing application and treatment at a reasonable pace and assuring a paste of stable quality and texture throughout the paste storage container.

In order to attain the above-stated objects, the present inventive paste compositions comprise in part a rubber component and a filler component, both components being free from organic solvents. The rubber component comprises a liquid rubber having an average molecular weight from about 1,000 to about 80,000 and a viscosity at 40° C. from about 200 poise to about 6,000 poise. The paste compositions contain a rubber component in amounts from about thirty percent to about seventy percent by weight of the composition.

Regarding the liquid rubber in the present invention, diene-type liquid rubber, especially butadiene-type liquid rubber, and isoprene-type liquid rubber may be used advantageously. A liquid rubber mix can be prepared by kneading a liquid rubber having an average molecular weight of about 80,000 or more with liquid rubbers of lower average molecular weight to yield a mix with an average molecular weight from about 1,000 to about 80,000. For example, a mixture obtained by kneading masticated natural rubber, isoprene rubber, styrene-butadiene rubber, butadiene rubber, or styrene-isoprene-styrene rubber with butadiene-type liquid rubber or isoprene-type liquid rubber may be used.

Regarding the filler component, known fillers which have been employed in a common tacky tape may also be used in the present paste composition in a powdery form. These known fillers include inorganic type fillers such as calcium carbonates, magnesium carbonates, silicates, silicic acids, aluminum hydrates, calcium sulfates, calcium sulfites and other calcium-type fillers. Alternatively, natural high molecular weight polymers such as starchs, mannans, marine plants, plant mucilages, micro-organism mucilages, proteins and celluloses may also be used. In addition, semi-synthetic water-soluble polymers such as semi-synthetic starchs, and synthetic water-soluble polymers such as polyvinyl alcohols, sodium polyacrylates, and polyethylene oxides, likewise may be used.

In the present invention such tackifiers as rosins, hydrogenated rosins, glyceral-esters, poly-terpene resins, terpene phenol resins, "Ca series" petroleum resins and alicyclic series hydrogenated petroleum resins optionally may be added to control the initial tackiness of the paste.

Also, moisturizing agents such as hyaluronic acid, sodium hyaluronate, collagen, carboxymethyl dextran, chitosan, squalane, or lecithin may be added.

Furthermore anti-oxidants, cross linking agents and coloring agents may be added to the present inventive paste compositions.

The paste compositions according to the present invention are prepared by supplying liquid rubber into a mixing device or blender, such as a pressure kneader, a kneader or a universal mixer. A filler component is gradually added with stirring to yield a homogeneous paste composition. When a plurality of filler components are added or when additional components such as anti-oxidants or color agents are added, it is recommended from an efficiency view point that they are previously mixed to homogeneity in a mixing device, such as a V-shaped blender or in a ball mill prior to their addition to the paste composition. Alternatively, they can be added in the order of their mixing ratio or mixability, with the components benefiting from greater mixing being added prior to the other components. When the present inventive liquid rubber based paste is prepared by kneading a rubber having a higher polymerization degree and a molecular weight above about 80,000 together with a rubber having a lower polymerization degree, into a mix having the preferred average molecular weight, it is desirable to blend homogeneously prior to the addition of the filler component. Blending of such rubbers can be done in a shorter period of time by heating while mixing. The thus prepared homogeneous paste composition can be packed in a small bottle or tube to facilitate handling of a necessary quantity at the time of application or treatment.

An important feature of the present inventive compositions is that the compositions comprise a liquid rubber component and a filler component free from any organic solvent. This organic solvent free composition prevents the stimulation and irritation of skin and mucosa normally found with conventional compositions, and maintains a stable paste condition, even when stored in an open container, without the solidifying which can occur with conventional compositions due to the evaporation of organic solvent out from conventional paste compositions.

When the liquid rubber to be added as part of the paste composition has a molecular weight less than 1,000, it has poor elastomer and cohesion properties and is less susceptible to form a paste-like form causing undesirable cold flow and cohesion rupture with the paste. On the contrary, when the molecular weight of the rubber is more than 80,000, elastomer and cohesion properties become too high and the composition will be too stiff and solid to form and maintain the proper paste consistency at room temperature. For the above reasons, the molecular weight of the liquid rubber is preferred if between about 1,000 and about 80,000 in the present invention.

In addition, when a liquid rubber has a viscosity at 40° C. of lower than about 200 poise, its liquid property becomes too great for this rubber to be cohesive, so that such a rubber fails to form a paste consistency even when included with a filler component. Whereas, when the viscosity at 40° C. of the rubber is higher than about 6,000 poise, the resulting composition is unable to form a paste at room temperature because of the rubber's high elastomeric property. Consequently in the present invention the preferred viscosity of the liquid rubber at 40° C. is set from about 200 to about 6,000 poise.

DESCRIPTION OF THE PREFERRED EMBODIMENTS

The present inventive paste compositions will be explained by Experiments and Comparative Examples set out below. Meanwhile, concentrations of the components listed in the experiments below represent parts by weight.

Butadiene-type liquid rubbers, including LCB by Nippon Zeon Co., NISSEKI LCB by Nippon Petrochemical, POLY BD by Idemitsu Petrochemical Co., SUMIKAOIL by Sumitomo Chemical Co., HYCAR by Ube Industries Co., and NISSO-PB by Nippon Soda, all having average molecular weights from about 550 to about 5,000, are applicable in the present composition. Isoprene-type liquid rubbers, such as KURAPRENE from Kuraray Co., which has an average molecular weight from about 30,000 to about 50,000 also may be applicable.

EXPERIMENT 1

50 parts of KURAPRENE LIR-50, a liquid isoprene rubber from Kuraray Co. having an average molecular weight of about 47,000 and a viscosity of about 4,800 poise at 40° C., 46 parts of CMC DAICEL 1190 sodium carboxymethylcellulose from Daicel Chemical Industries Co., and 4 parts of AEROSIL 300 silica from Japan Aerosil were fed into a pressure kneader and subjected to a kneading for 5 minutes to obtain a skin barrier paste composition.

EXPERIMENT 2

55 parts of KURAPRENE LIR-30, a liquid isoprene rubber from Kuraray Co. having an average molecular weight of 29,000 and a viscosity of 740 poise at 40° C., 40 parts of karaya gum and 5 parts of AEROSIL 200 silica from Japan Aerosil were fed into a pressure kneader and subjected to kneading for 5 minutes to obtain another skin barrier paste composition.

EXPERIMENT 3

65 parts of KURAPRENE LIR-503 liquid isoprene rubber from Kuraray Co. having an average molecular weight of 25,000 and a viscosity of 3,500 poise at 40° C., 25 parts of PHARMACOPOEIA CMC DAICEL 1290J sodium carboxymethylcellulose from Daicel Chemical Industries Co., 5 parts of MEDICAL GRADE GELATIN R from Nitta Gelatin, and 5 parts of HERBSTREITHPECTIN LM PECTIN from Herbstreith K.C. were fed into a pressure kneader and subjected to kneading for 5 minutes to obtain a skin barrier paste composition.

EXPERIMENT 4

50 parts of NISSEKI HV 1900 liquid polybutene from Nippon Petrochemical having an average molecular weight of 2,700 and a viscosity of 1,710 poise at 40°

C., 30 parts of PHARMACOPOEIA CMC DAICEL 1920J sodium carboxymethylcellulose from Daicel Chemical Industries Co., 10 parts of zinc oxide, and 10 parts of aluminum hydroxide were fed into a pressure kneader and subjected to kneading for 5 minutes to obtain another skin barrier paste composition.

EXPERIMENT 5

40 parts of TETRAX 3T polyisoprene from Nippon Petrochemicals having an average molecular weight of 30,000, and 60 parts of NISSEKI POLYBUTENE LV 100 polybutene from Nippon Petrochemicals having an average molecular weight of 500 were kneaded in a pressure kneader for 5 minutes to yield a liquid rubber having an average molecular weight of 15,000 and a viscosity of 4,500 poise at 40° C. To 40 parts of this prepared liquid rubber, 30 parts of PHARMACOPOEIA CMC DAICEL 1290J sodium carboxymethylcellulose from Daicel Chemical Industries Co., and 20 parts of karaya gum were combined in the kneader and subjected to kneading for 5 minutes to obtain a skin barrier paste composition.

EXPERIMENT 6

10 parts of QUINTAC 3421 SIS from Nippon Zeon Co., 30 parts of liquid polyisoprene rubber having an average molecular weight of 2,900, and 20 parts of tackifier Resin PX from Yasuhara Yushi were fed into a pressure kneader and subjected to kneading for 5 minutes to yield a homogeneous liquid rubber having an average molecular weight of 80,000 and a viscosity of 5,500 poise at 40° C. To 60 parts of this prepared liquid rubber, 47 parts of PHARMACOPOEIA 1290J sodium carboxymethylcellulose from Daicel Chemical Industries Co., and 3 parts of AEROSIL 300 silica from Japan Aerosil were combined in a kneader and subjected to kneading for 5 minutes to obtain a skin barrier paste composition.

COMPARATIVE EXAMPLE 1

60 parts of SUMIKAOIL 150 liquid polybutene from Sumitomo Chemical Co. having an average molecular weight of 1,700 and a viscosity of 7.5 poise at 40° C., 55 parts of PHARMACOPOEIA GRADE CMC DAICEL 1290J sodium carboxymethylcellulose from Daicel Chemical Industries Co., and 5 parts of AEROSIL 300 silica from Japan Aerosil were fed into a pressure kneader and subjected to a kneading for 5 minutes to obtain a comparative skin barrier paste composition.

COMPARATIVE EXAMPLE 2

20 parts of KURAPRENE LIR-30 liquid isoprene rubber from Kuraray Co. having an average molecular weight of 29,000, 65 parts of PHARMACOPOEIA GRADE CMC DAICEL 1290J sodium carboxymethylcellulose from Daicel Chemical Industries Co., and 5 parts of AEROSIL 300 silica from Japan Aerosil were fed into a pressure kneader and subjected to kneading for 5 minutes to obtain a comparative skin barrier paste composition.

COMPARATIVE EXAMPLE 3

80 parts of Kuraprene LIR-30 liquid isoprene rubber from Kuraray Co. having an average molecular weight of 29,000, 15 parts of PHARMACOPOEIA GRADE CMC DAICEL 1290J sodium carboxymethylcellulose from Daicel Chemical Industries Co., and 5 parts of AEROSIL 300 silica from Japan Aerosil were fed into a pressure kneader and subjected to kneading for 5 minutes to obtain a comparative skin barrier paste composition.

COMPARATIVE EXAMPLE 4

45 parts of TETRAX 4T polyisoprene from Nippon Petrochemicals having an average molecular weight of 50,000, 20 parts of karaya gum, 16 parts of MEDICAL GRADE GELATIN R by Nitta Gelatin, 16 parts of guar gum, and 3 parts of AEROSIL 300 silica from Japan Aerosil were fed into a pressure kneader and subjected to kneading for 8 minutes to obtain a comparative skin barrier paste composition.

COMPARATIVE EXAMPLE 5

60 parts of PVP-K SERIES polyvinylpyrrolidone from GAF (including isopropanol), 40 parts of karaya gum (150 mesh), and 20 parts of ethyleneglycol were fed into a universal mixer and subjected to kneading for 3 minutes to obtain a comparative skin barrier paste composition.

COMPARATIVE EXAMPLE 6

20 parts of GANTREZ ES 425 by GAF, a 50% solution of methyl vinyl ether/butyl monoester of maleic anhydride copolymer in ethanol, 4 parts of AEROSIL 300 silica from Japan Aerosil, 36 parts of karaya gum 150 mesh, 7 parts of glycerol serving as an organic solvent, 0.14 parts of methylparaben solution and 0.06 parts of butylparaben solution both serving as a germicide were fed into a universal mixer and subjected to kneading to obtain a homogeneous comparative skin barrier paste composition.

The paste products thus obtained through the above inventive Experiments and Comparative Examples were examined in terms of the preferred properties of the present invention, namely:

(1) ease of removal from a container in necessary quantities by means of fingertips or a spatula;

(2) formability with fingertips so as to adjust to the skin stoma section or opening;

(3) adjustability and adhesiveness to the skin as well as to the adhesive plate of the excretion or exudation pouch means employed;

(4) ability to maintain seal without paste dissolution or cold flow when applied and throughout the application period;

(5) removability of the adhesive and the adhesive plate of the secured excretion or exudation collection means when the intent of the application is achieved, or when a replacement of the attached means is needed or when stoma observation becomes necessary; and (6) Reduced irritation when applied to the skin surrounding a stoma.

The results obtained are as follows:

The paste compositions in accordance with Experiments 1–6 could be removed easily in necessary quantities from a container by means of fingertips or an appliance such as an ointment spatula, and could be formed into the shape of the applied skin section with fingertips without excessive tackiness or adhesion to the fingertips. Also the pastes fitted evenly and were sufficiently tacky and adhesive to the skin or the skin adhesive plate of the excretion or exudation collection means and caused no leakage of the excretion or exudation. Further, pastes from Experiments 1–6 were serviceable during the application period without any irritation to the skin or mucosa, therefore resulting in a comfortable application through to the end of the treatment. Furthermore, pastes 1-6 could be removed easily from the skin with no pain and no paste residue, and from the skin adhesive plate as well.

Contrary to the results from pastes associated with Experiments 1-6, the paste composition of Comparative Example 1 showed excessive cohesion presumably by the liquid rubber component, leading to an unsatisfactory formation and elevated tackiness to fingertips during paste application. Also its durability was poor which caused leakage around the excretion or exudation collector means resulting in a short service period. At the time of removal, the paste composition remained on the skin around the stoma, which was troublesome and required an additional cleaning treatment.

The paste product of Comparative Example 2 was deficient in the liquid rubber component so that it caused cracking during the forming operation and was incapable of properly forming the needed seal. It adhered very poorly to the skin around the stoma and to the skin adhesive plate of the collection means, thus lacking the necessary sealing property.

The paste composition of Comparative Example 3 had too great a ratio of the liquid rubber relative to the filler component so that it showed rubber properties predominantly, such as it formed a hard paste at low temperatures and failed to maintain a shape formed by the paste when subject to high temperatures resulting in a cold flow. Additionally, the paste adhered excessively and it was difficult to remove the paste from the skin or the skin adhesive plate.

The product of Comparative Example 4 was stiff to form with the fingertips at room temperatures because of the high viscosity of the polyisoprene, a component of the liquid rubber.

The paste compositions of Comparative Examples 5 and 6 contained an organic solvent and yielded an intense irritation of the contacted skin, causing dermatitis and pain. Further, pastes 5 and 6 changed viscosity during formation and application with fingertips. Namely, they were initially too soft, then became harder with time, eventually becoming difficult to work with and form.

EFFECT OF THE INVENTION

The present invention therefore provides paste compositions less irritating to the skin, mucosa and injured area, thus assuring prolonged safe use without causing dermatitis. Also, the present inventive paste compositions have excellent formability properties so that a secure seal between the stoma and the collection means can be formed with the fingertips to attain a complete and reliable skin barrier. Further the present inventive composition has such an appropriate tackiness as to show satisfactory adhesion to the skin and to the skin adhesive plate of the collection means, yet is readily removable without causing excessive discomfort and pain to the patient.

Thus there has been shown and described novel means for skin barrier paste compositions. The present invention fulfills all the objects and advantages set forth above. It will be apparent to those skilled in the art, however, that many changes, modifications, variations and other uses and applications which do not depart from the spirit and scope of the invention are deemed covered by the invention which is limited only by the claims which follow.

What is claimed is

1. An adhesive skin barrier paste composition comprising at least an organic solvent free rubber component and an organic solvent free filler component, said rubber component being between about 30% by weight and about 70% by weight of the composition and consisting of at least 30% polyisoprene liquid rubber characterized by having an average molecular weight of between about 1,000 and about 80,000, and having viscosity from about 200 to about 6,000 poise at 40 degrees C., said composition being capable of being fitted evenly to the skin, sufficiently tacky to provide secure adhesion of an exudate or excrement collection appliance to the skin without leakage therebetween, non-irritating to the skin and mucosa, and easily removable without leaving a paste residue.

2. The adhesive skin barrier paste composition of claim 1 wherein the filler component is selected from the group consisting of inorganic type fillers, natural polymers, semi-synthetic water-soluble polymers and synthetic water-soluble polymers.

3. The adhesive skin barrier paste composition of claim 1 wherein the liquid rubber component includes a mixture of rubber.

* * * * *